United States Patent
Murpani et al.

(10) Patent No.: US 10,507,204 B2
(45) Date of Patent: Dec. 17, 2019

(54) PHARMACEUTICAL COMPOSITION COMPRISING AMORPHOUS LENALIDOMIDE

(71) Applicant: SYNTHON B.V., Nijmegen (NL)

(72) Inventors: Deepak Murpani, Nijmegen (NL); Marta Vivancos Martinez, Sant Boi de Llobregat (ES); Lisardo Alvarez Fernandez, Sant Boi de Llobregat (ES); Luis Nogueiras Nieto, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 15/537,857

(22) PCT Filed: Dec. 16, 2015

(86) PCT No.: PCT/EP2015/080060
§ 371 (c)(1),
(2) Date: Jun. 19, 2017

(87) PCT Pub. No.: WO2016/097030
PCT Pub. Date: Jun. 23, 2016

(65) Prior Publication Data
US 2017/0368048 A1 Dec. 28, 2017

(30) Foreign Application Priority Data
Dec. 19, 2014 (WO) ............... PCT/EP2014/078824

(51) Int. Cl.
| A61K 31/454 | (2006.01) |
| A61K 9/14 | (2006.01) |
| A61K 9/16 | (2006.01) |
| A61K 9/48 | (2006.01) |

(52) U.S. Cl.
CPC ............ *A61K 31/454* (2013.01); *A61K 9/143* (2013.01); *A61K 9/1611* (2013.01); *A61K 9/4866* (2013.01)

(58) Field of Classification Search
CPC ..................................... A61K 9/143
See application file for complete search history.

(56) References Cited

U.S. PATENT DOCUMENTS 10,328,028 B2 * 6/2019 Vivancos Martinez ............... A61K 9/1617
2012/0046315 A1 2/2012 Rimkus et al.

FOREIGN PATENT DOCUMENTS

| EP | 925294 B1 | 12/2002 |
| EP | 2238979 | 10/2010 |
| EP | 2875817 | 5/2015 |
| WO | WO2005023192 | 3/2005 |
| WO | WO 2009114601 | 9/2009 |
| WO | WO2010054833 | 5/2010 |
| WO | WO2011111053 | 9/2011 |
| WO | WO 2011154009 | 12/2011 |
| WO | WO 2015078845 | 6/2015 |
| WO | WO 2015124496 | 8/2015 |

OTHER PUBLICATIONS

"Neusilin: The extraordinary excipient for oral solid dosage forms", Fuji Chemical Industry Co., LTD, Technical Newsletter, Oct. 2007.*

* cited by examiner

*Primary Examiner* — Gina C Justice
(74) *Attorney, Agent, or Firm* — Buscher Patent PLLC

(57) ABSTRACT

The present invention relates to a pharmaceutical composition comprising an amorphous adsorbate of lenalidomide, or a pharmaceutically acceptable salt thereof, on a porous carrier and one or more pharmaceutically acceptable excipients. The invention further relates to the use of said composition as a medicament, particularly in the treatment of multiple myeloma and myelodysplastic syndromes.

11 Claims, No Drawings

PHARMACEUTICAL COMPOSITION COMPRISING AMORPHOUS LENALIDOMIDE

BACKGROUND OF THE PRESENT INVENTION

Lenalidomide, chemically (RS)-3-(4-Amino-1-oxo 1,3-dihydro-2H-isoindol-2-yl)piperidine-2,6-dione of formula (I),

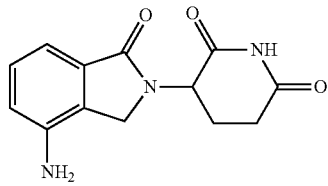 [SMILES: Nc1cccc2c1CN(C1CCC(=O)NC1=O)C2=O]

is a pharmaceutically active compound used for the treatment of multiple myeloma and myelodysplastic syndromes The compound was discovered by Celgene and is disclosed in EP925294. Lenalidomide is the active ingredient in the medicinal product sold under the brand name Revlimid®.

Lenalidomide exhibits polymorphism. WO2005023192 discloses crystalline forms of lenalidomide, its process of preparation, compositions comprising these crystalline forms and its use for treatment of diseases. Polymorph B is the most stable form and is present in the marketed tablets. Compositions comprising both amorphous and crystalline lenalidomide are also disclosed in this application. Other polymorphic forms of lenalidomide are disclosed in WO2011111053. The prior art thus teaches that lenalidomide crystallizes very easily. Moreover, it was experienced in our laboratory that polymorphic transitions of lenalidomide take place rather easily, especially in drug product.

Lenalidomide is slightly soluble in water. Conventional approaches to increase solubility consist on micronizing the API. Nevertheless, it was experienced in our laboratory that micronization of lenalidomide gave partially amorphous solid, which readily converts to other crystalline forms. It is known that generally the solubility of amorphous forms is higher compared to the solubility of crystalline forms. In view of this, it would be desirable to produce stable amorphous lenalidomide and to find a robust process for making such a stable amorphous lenalidomide.

WO2010054833 and WO 2009114601 discloses solid dispersions containing amorphous lenalidomide.

Thus in view of the prior art cited above, there is still a need for alternative pharmaceutical compositions comprising lenalidomide, or a pharmaceutically acceptable salt thereof, which are stable and suitable for use on a commercial scale.

BRIEF DESCRIPTION OF THE PRESENT INVENTION

The present invention provides an amorphous adsorbate of lenalidomide, or a pharmaceutically acceptable salt thereof, on a porous carrier.

It also provides pharmaceutical composition comprising an amorphous adsorbate of lenalidomide, or a pharmaceutically acceptable salt thereof, on a porous carrier and one or more pharmaceutically acceptable excipients.

It also provides a process for preparing said adsorbate by combining lenalidomide, or a pharmaceutically acceptable salt thereof, with a porous carrier and adding a suitable solvent or solvent mixture, followed by evaporation of the solvent(s).

Additionally, the invention provides a process for preparing said pharmaceutical composition comprising mixing or granulating said adsorbate with one or more excipients, followed by encapsulation.

Said pharmaceutical composition may be used as a medicament, particularly in the treatment of multiple myeloma and myelodysplastic syndromes.

DETAILED DESCRIPTION OF THE PRESENT INVENTION

The present invention relates to a pharmaceutical composition comprising an adsorbate of lenalidomide, or a pharmaceutically acceptable salt thereof, on a porous carrier and one or more pharmaceutically acceptable excipients.

Drugs that can exist in either an amorphous or crystalline form tend to crystallize over time when present in an amorphous state because the crystalline form of the drug is a lower-energy state than the amorphous form. Surprisingly, the adsorbate of the present invention containing lenalidomide, or a pharmaceutically acceptable salt thereof, is present in a stabilized amorphous form, which means that during stability studies no conversion into any crystalline form was observed even under stress conditions.

The weight ratio of lenalidomide, or a pharmaceutically acceptable salt thereof, to porous carrier in the adsorbate ranges from about 1:1 to about 1:5, preferably from 1:1 to 1:3.

A porous carrier has an outer and/or inner surface onto which the lenalidomide or a pharmaceutically acceptable salt thereof, can be adsorbed.

The porous carrier has a high surface area, meaning that the carrier has a surface area of at least 20 $m^2/g$, preferably at least 50 $m^2/g$, more preferably at least 100 $m^2/g$, and most preferably at least 180 $m^2/g$. The surface area of the porous carrier may be measured using standard procedures. One exemplary method is by low-temperature nitrogen adsorption, based on the Brunauer, Emmett and Teller (BET) method, well known in the art.

The porous carrier is selected from the group consisting of metal oxides, metal silicates, metal phosphates, metal carbonates, zeolites and molecular sieves. More preferably the porous carrier is a metal oxide. Examples of suitable metal oxides are silicon dioxide, titanium dioxide, zinc dioxide, zinc oxide and aluminium oxide. Most preferred, the porous carrier is porous silicon dioxide, also known as silica. Typical examples of commercially available silicas are Syloid® XDP 3050 and Syloid® XDP 3150, characterized by a pore volume of >1.70 ml/g and an average particle size of 48-66 microns and 120-170 microns respectively. The aforementioned silicas Syloid® XDP 3050 and Syloid® XDP 3150 have typical surface areas of 320 $m^2/g$.

At least a major portion of lenalidomide or a pharmaceutically acceptable salt thereof, in the adsorbate is amorphous. The term "a major portion" of lenalidomide, or a pharmaceutically acceptable salt thereof, means that at least 60% of the drug is in amorphous form, rather than a crystalline form. Preferably, lenalidomide, or a pharmaceutically acceptable salt thereof, in the adsorbate is at least 80% in amorphous form. More preferably, lenalidomide, or a pharmaceutically acceptable salt thereof, in the adsorbate is "almost completely amorphous" meaning that the amount of lenalidomide, or a pharmaceutically acceptable salt thereof, in the amorphous form is at least 90% as measured by powder X-ray diffraction or any other standard quantitative measurement. Most preferably, lenalidomide, or a pharmaceutically acceptable salt thereof, in the adsorbate is in a completely amorphous form within the detection limits of the techniques used for characterization, like powder X-ray diffraction.

The adsorbate in accordance with the present invention advantageously is in the form of a free-flowing powder, with excellent handling properties and stable morphology. The adsorbate is very suitable to be used for the preparation of pharmaceutical compositions.

The pharmaceutical compositions of the present invention comprise the adsorbate of lenalidomide, or a pharmaceutically acceptable salt thereof, on a porous carrier and one or more pharmaceutically acceptable excipients. The excipients to be used in accordance with the present invention are well-known to and are those excipients which are conventionally used by the person skilled in the art. Depending on the dosage form chosen for the pharmaceutical composition, the person skilled in the art will be able to select suitable pharmaceutically acceptable excipients. Preferably, the pharmaceutically acceptable excipients are chosen from one or more binders, diluents, disintegrants, glidants, lubricants, stabilizers, surface active agents or pH-adjusting agents.

The pharmaceutical compositions of the present invention display dissolution behaviour typical for immediate-release formulations. During preparation and storage of the pharmaceutical compositions of the present invention, the adsorbate of lenalidomide, or a pharmaceutically acceptable salt thereof, on a porous carrier remains in the amorphous form.

The methods and equipment to carry out the process to form the adsorbate are well known in the art.

One possible method is combining lenalidomide, or a pharmaceutically acceptable salt thereof, with a porous carrier and adding a suitable solvent or solvent mixture, followed by evaporation of the solvent(s). Examples of equipments that can be used are fluid bed, high shear mixed and spray drying. Spray dryer is preferred because promotes a rapid evaporation of the solvent. The rapid evaporation of the solvent prevents crystallization. When the fluid bed technology is used additionally a pharmaceutical carrier is needed. Lactose, cellulose, starch and phosphates are the preferred pharmaceutical carriers. Pregelatinized starch, MCC and calcium phosphate are the most preferred pharmaceutical carriers. Even most preferred is calcium phosphate, which gives particularly good results.

Preferably, the solvent or solvent mixture is acidic water, a polar organic solvent or a mixture of acidic water and a polar organic solvent. Preferred ratio organic solvent:acidic water is 7:3 (w/w). In an advantageous variant of the process of the present invention, lenalidomide, or a pharmaceutically acceptable salt thereof, is dissolved in acidic water or a mixture of acidic water and a polar organic solvent and the porous carrier is added to this solution. Preferred ratio organic solvent:acidic water is 7:3 (w/w). Preferred polar organic solvents are alcohols, particularly ethanol or methanol, ethers, particularly tetrahydrofuran, ketones, particularly acetone and acetonitrile. Preferably, 0.1N aqueous HCl or a mixture of acetone and 0.1N aqueous HCl is used. Preferred ratio of acetone:0.1N aqueous HCl is 7:3 (w/w). This ratio gives an optimal impurity profile.

The adsorbate can also be prepared by cogrinding lenalidomide, or a pharmaceutically acceptable salt thereof, with a porous carrier, for example using a ball mill. This process to prepare the adsorbate can be carried out without the use of solvents. This process is economically preferred and more environmentally friendly.

Another method to prepare an adsorbate of lenalidomide, or a pharmaceutically acceptable salt thereof, on a porous carrier, comprises a thermal process. Here, lenalidomide, or a pharmaceutically acceptable salt thereof, is melted and then applied on the porous carrier, for example in a thin-screw extruder.

The carrier is insoluble in the process environment used to form the adsorbate. That is, where the adsorbate is formed by solvent processing, the carrier does not dissolve in the solvent. Where the adsorbate is formed by a melt or thermal process, the carrier has a sufficiently high melting point that it does not melt.

The present invention still further provides a process to prepare pharmaceutical compositions comprising an adsorbate of lenalidomide, or a pharmaceutically acceptable salt thereof, on a porous carrier and one or more pharmaceutically acceptable excipients. The process comprises mixing or granulating the adsorbate with one or more pharmaceutically acceptable excipients, followed by encapsulation, using equipment and methods well-known to the skilled artisan.

In an advantageous variant of the process of the present invention, a solution of lenalidomide, or a pharmaceutically acceptable salt thereof, and the porous carrier was sprayed over the pharmaceutical carrier e.g. the diluent, in a fluidized bed and the resulting granulate/blend was mixed with one or more pharmaceutically acceptable extragranular excipients, followed by encapsulation. Preferably, a solution of lenalidomide and porous carrier in 0.1N aqueous HCl 7:3 (w/w) was sprayed over calcium phosphate in a fluidized bed, after which the granulate/powder blend was mixed with microcrystalline cellulose, croscarmellose sodium and magnesium stearate, followed by encapsulation. Preferably, HPMC or gelatin capsules are used.

The pharmaceutical compositions of the present invention are packaged in blister pack material. The blister pack materials to be used in accordance with the present invention may be any blister pack material known to a person of ordinary skill in the art. Suitable blister pack materials to be used in accordance with the present invention are selected from the group of Aclar, PVC/Alu, Duplex/Alu, Triplex/Alu and Alu/Alu. To ensure protection of the compositions of the present invention from e.g. moisture and thereby preventing polymorphic conversions, Aclar, Triplex/Alu and Alu/Alu are particularly preferred blister pack materials The pharmaceutical composition in accordance with the present invention may be used as a medicament. The pharmaceutical composition typically may be used in the treatment of treatment of multiple myeloma and myelodysplastic syndromes The present invention is illustrated by the following Examples.

EXAMPLES

Example 1, Lenalidomide:Syloid XDP 3050
(Weight Ratio 1:3)

4 g of lenalidomide is dissolved in 175 ml of acetone:0.1N HCl (70:30) under stirring conditions at 50° C.; subsequently 12 g Syloid XDP 3050 are incorporated; this excipient is suspended in the solution. Once the suspension is homogenous and the spray-drier is preheated, the solution is pumped into the spray-drier, where the solvent is instantaneously evaporated and the solid product is collected.

XRPD data showed that the isolated adsorbate was fully amorphous.

Example 2, Lenalidomide:Syloid XDP 3050 (Weight Ratio 1:2)

55.56 g of lenalidomide is dissolved in 2250 ml of acetone:0.1N HCl 7:3 (w/w) under stirring conditions at 50° C.; afterwards 111.1 g of Syloid XDP 3050 are incorporated and this excipient remains in suspension. Once the suspension is homogenous and the fluid bed is preheated, the solution is pumped into the fluid bed, where it is spray-dried over a carrier excipient (e.g. calcium phosphate). Process parameters are adjusted to obtain an optimum spray-dying process by having a fast, instantaneous solvent evaporation.

XRPD data showed that the isolated adsorbate was fully amorphous.

Example 3, Lenalidomide:Syloid XDP 3050

1 part of lenalidomide is mixed together with 1 or 5 parts of Syloid XDP 3050. The mixture is homogenized and subsequently ball-milled at 25 osc/sec for at least one hour.

XRPD data showed that the isolated adsorbate was fully amorphous.

Example 4, Lenalidomide:Syloid XDP 3050 (Weight Ratio 1:1)

42.55 g of lenalidomide is dissolved in 1725 ml of acetone:0.1N HCl 7:3 (w/w) under stirring conditions at 50° C. Once lenalidomide is completely dissolved, 42.55 g of Syloid XDP 3050 is added to the solution. The suspension, which is kept under stirring and heating conditions, is then sprayed over 568 g of anhydrous calcium phosphate (71%) in the fluid bed, evaporating the solvent. The resulting granulate/blend is dried in the fluid bed.

This granulate is sieved and subsequently mixed with 114.88 grams of microcrystalline cellulose (14.36% total weight) and 24 grams of sodium croscarmellose (3% total weight), followed by the addition of 8 grams of magnesium stearate (1% total weight).

The powder blend obtained is encapsulated in size-0 gelatine or HPMC capsules. Capsules with a total weight of powder blend of 500 mg, containing 25 mg of lenalidomide are obtained.

The invention claimed is:

1. A pharmaceutical composition comprising (i) an amorphous adsorbate of lenalidomide, or a pharmaceutically acceptable salt thereof, on a porous carrier and (ii) one or more pharmaceutically acceptable excipients.

2. The composition according to claim 1, wherein the porous carrier is selected from the group consisting of metal oxides, metal silicates, metal phosphates, metal carbonates, zeolites and molecular sieves.

3. The composition according to claim 1, wherein the porous carrier has a surface area of at least 180 m$^2$/g.

4. The composition according to claim 1, wherein the porous carrier is a porous metal oxide.

5. The composition according to claim 1, wherein the porous carrier is porous silicon dioxide.

6. The composition according to claim 5, wherein said porous silicon dioxide has an average particle size within the range of 48-66 microns or 120-170 microns.

7. The composition according to claim 1, wherein the weight ratio of lenalidomide, or a pharmaceutically acceptable salt thereof, to porous carrier ranges from 1:1 to 1:5.

8. The composition according to claim 1, wherein the pharmaceutically acceptable excipients are one or more binders, diluents, disintegrants, glidants, lubricants, stabilizers, surface active agents or pH-adjusting agents.

9. An adsorbate of lenalidomide, which comprises a porous carrier having amorphous lenalidomide adsorbed thereto.

10. The adsorbate according to claim 9, wherein said porous carrier is porous silicon dioxide.

11. The adsorbate according to claim 10, wherein said porous silicon dioxide has an average particle size within the range of 48-66 microns or 120-170 microns.

* * * * *